United States Patent [19]

Wells et al.

[11] Patent Number: 4,567,368
[45] Date of Patent: Jan. 28, 1986

[54] BIPOLAR PULSED ELECTRON CAPTURE DETECTORS

[75] Inventors: Gregory J. Wells, Suisan; Richard K. Simon, Pittsburg, both of Calif.

[73] Assignee: Varian Associates, Inc., Palo Alto, Calif.

[21] Appl. No.: 571,989

[22] Filed: Jan. 19, 1984

[51] Int. Cl.[4] ............................................. G01N 27/66
[52] U.S. Cl. ................... 250/379; 250/382; 250/386; 250/384
[58] Field of Search ............... 250/423 P, 382, 386, 250/379, 389, 385, 387, 381, 375; 324/464, 465, 469; 422/90

[56] References Cited

U.S. PATENT DOCUMENTS

| | | | |
|---|---|---|---|
| Re. 28,951 | 8/1976 | Marshall, III et al. | 250/386 |
| 2,950,387 | 8/1960 | Brubacker | 250/423 P |
| 3,634,754 | 1/1972 | Lovelock | 324/465 |
| 3,892,968 | 7/1975 | Lovelock | 250/389 |
| 4,063,156 | 12/1977 | Patterson | 324/465 |
| 4,117,332 | 9/1978 | Felton et al. | 250/386 |

OTHER PUBLICATIONS

Lovelock, "The Electron Capture Detector Theory and Practice", J. Chromatography, 99, 1974, pp. 3–12.
Lovelock et al., "Electron-Capture Detector Theory and Practice", J. Chromatography, 158, 1978, pp. 123–138.

*Primary Examiner*—Carolyn E. Fields
*Attorney, Agent, or Firm*—Stanley Z. Cole; Keiichi Nishimura; Peter J. Sgarbossa

[57] ABSTRACT

In operating an ECD in constant current mode, two pulses are implemented either to the same electrode or to separate electrodes, thereby dispersing the space charge sheath near the collector electrode and thus enhancing electron extraction at high frequencies. This has the effect of extending both the dynamic range and the linear dynamic range.

30 Claims, 15 Drawing Figures

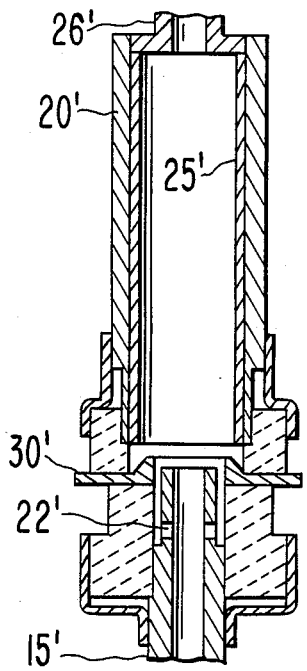
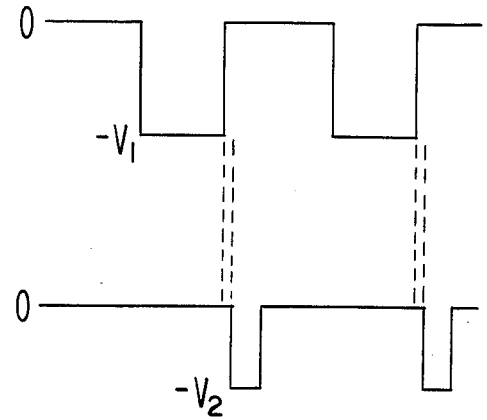
FIG. 7
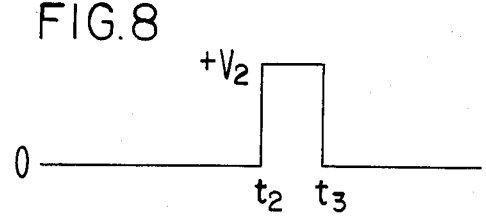
FIG. 8
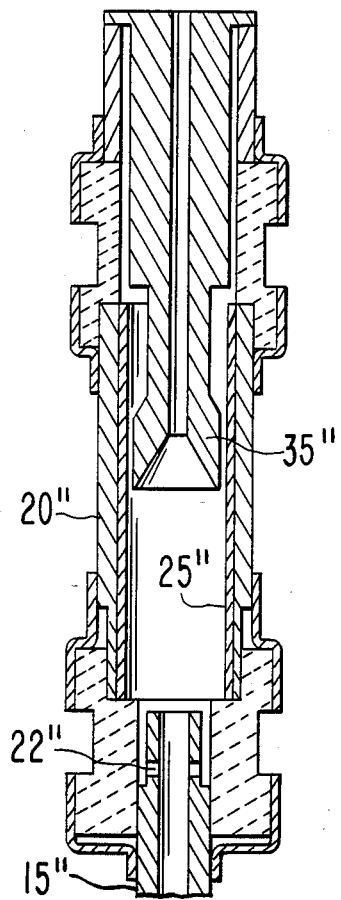
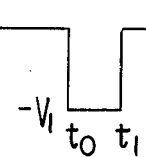

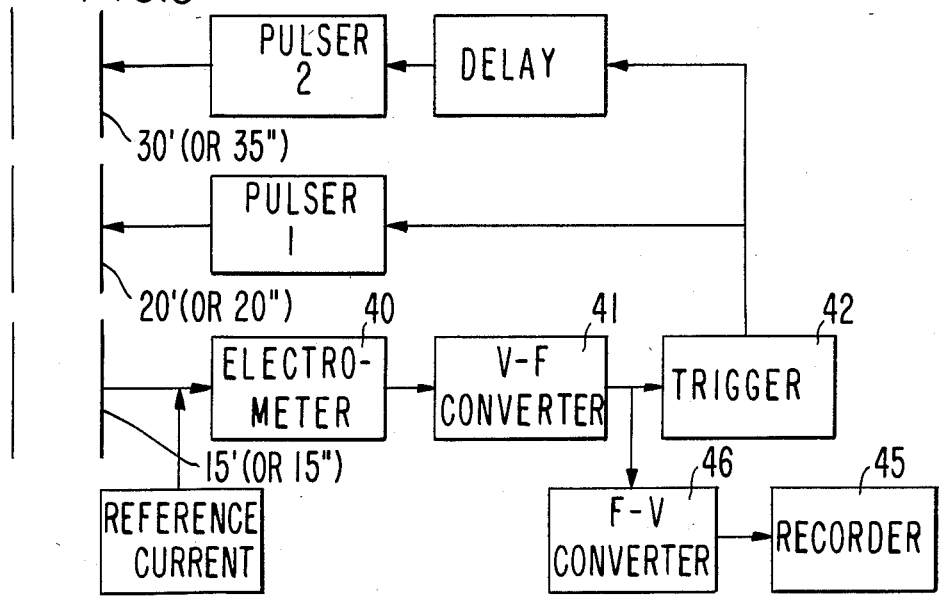
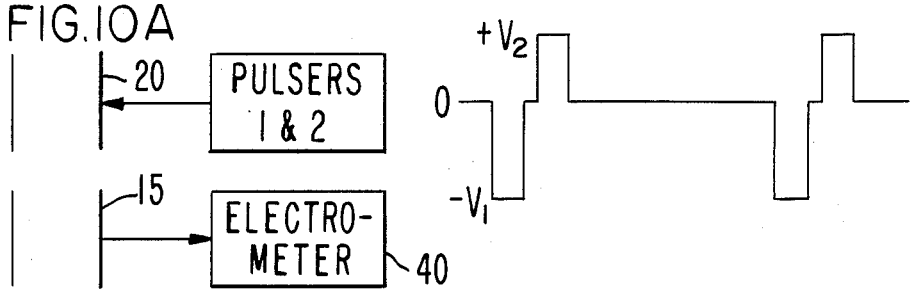
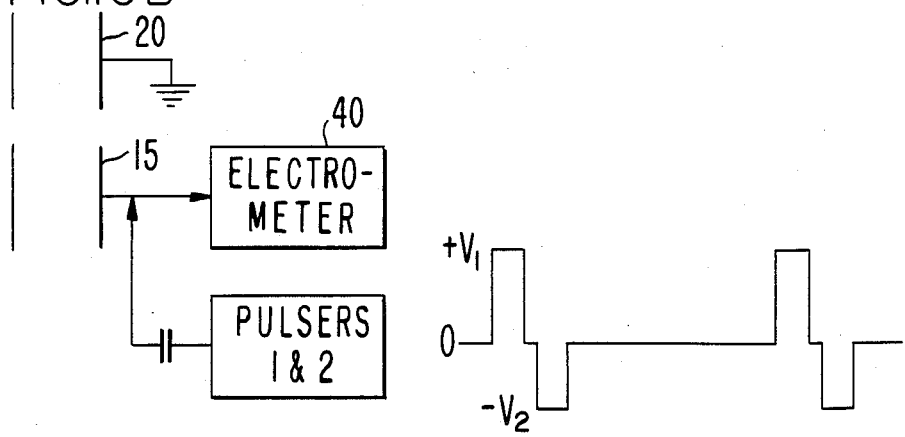

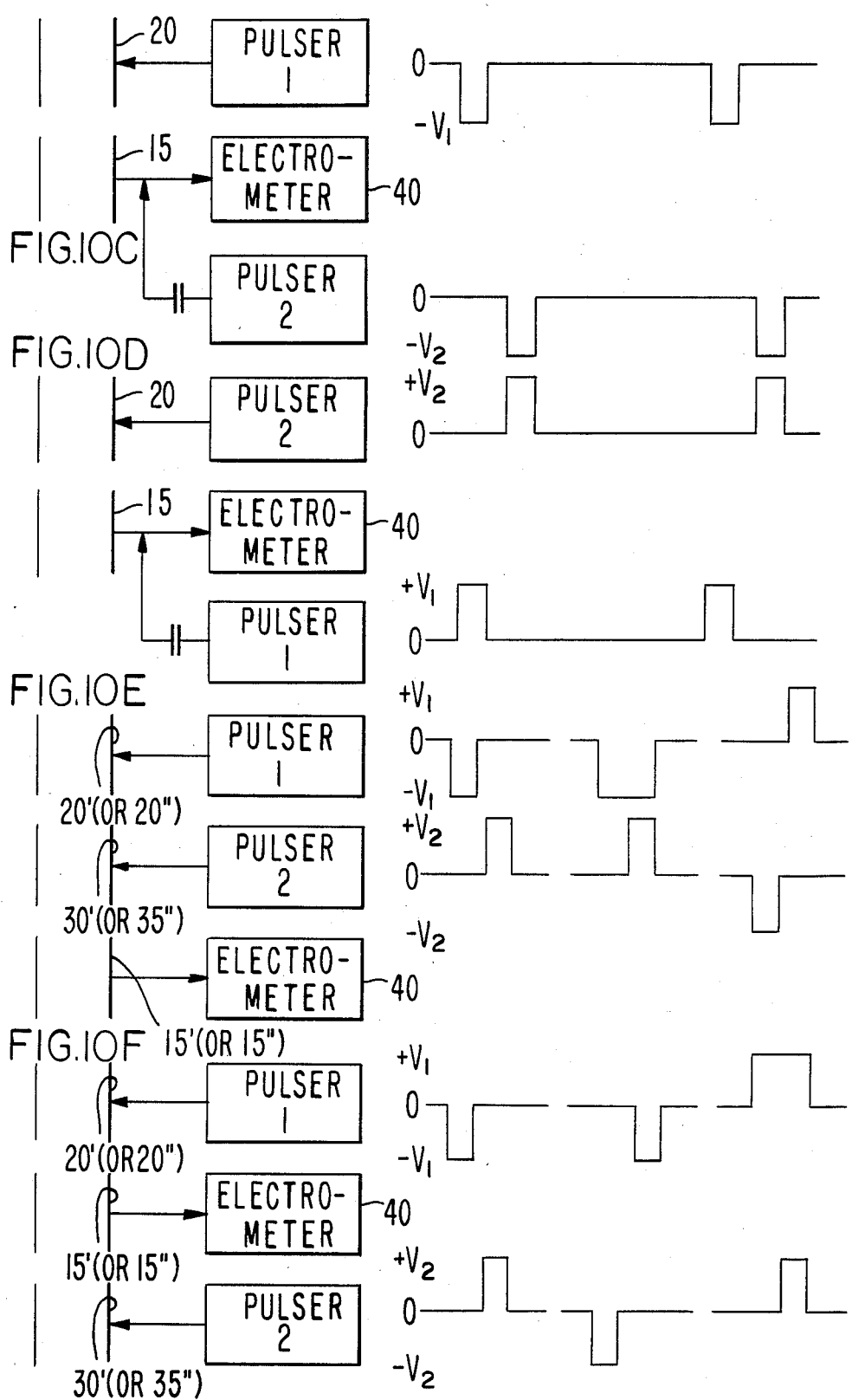

BIPOLAR PULSED ELECTRON CAPTURE DETECTORS

BACKGROUND OF THE INVENTION

This invention relates generally to a method of operating an electron capture detector (ECD) which provides a greatly increased linear dynamic range and more particularly to an ECD designed for application of bipolar pulses to enhance electron extraction at high frequencies.

By the electron capture detector technique in gas chromatography, a radiation source such as a radioactive foil ionizes the molecules of a carrier or make-up gas as it flows through the detector and the slow electrons thus produced are caused to migrate to the anode, forming a steady or pulsed current. This detector current becomes reduced if a sample containing electron-absorbing molecules is introduced and this loss of current is amplified by an electrometer and is analyzed.

Since its first introduction in 1960, the ECD has claimed advantages in its high specificity and sensitivity, but they have equally been plaqued by the lack of linear dynamic range. A new mode of operation for the ECD was proposed by Maggs, et al. (Analytical Chemistry, 43 1966 (1971)) according to which a constant current is maintained by changing the frequency of applied pulses, the theory being that the change in pulse frequency is proportional to the concentration of the electron-capturing species present within the ECD. In practice, however, the constant current mode is non-linear at frequencies exceeding 80 KHz. This may be due to collection of anions as well as electrons near the collector. Effects of applied fields on positive ions in the pulsed ECD have been considered generally, for example, by Connolly, et al, (J. of Chromatography, 265 145 (1983)).

SUMMARY OF THE INVENTION

It is therefore an object of the invention to provide a method of operating an ECD in gas chromatography by which both the dynamic range and the linear dynamic range can be extended.

It is another object of this invention to provide an ECD for operating in a bipolar pulse mode in order to enhance electron extraction at high frequencies.

BRIEF DESCRIPTION OF THE DRAWINGS

FIG. 7 is a schematic cross-sectional view of an ECD for bipolar pulsing with separate electrodes.

FIG. 8 is a schematic cross-sectional view of another type of ECD for bipolar pulsing with separate electrodes.

FIG. 9 is a block diagram of electronic components for providing bipolar pulsing to an ECD with separate electrodes.

FIG. 10 shows typical bipolar pulse profiles which may be applied to an ECD and arrangements of electronic components therefor.

DETAILED DESCRIPTION OF THE INVENTION

Figure 1:
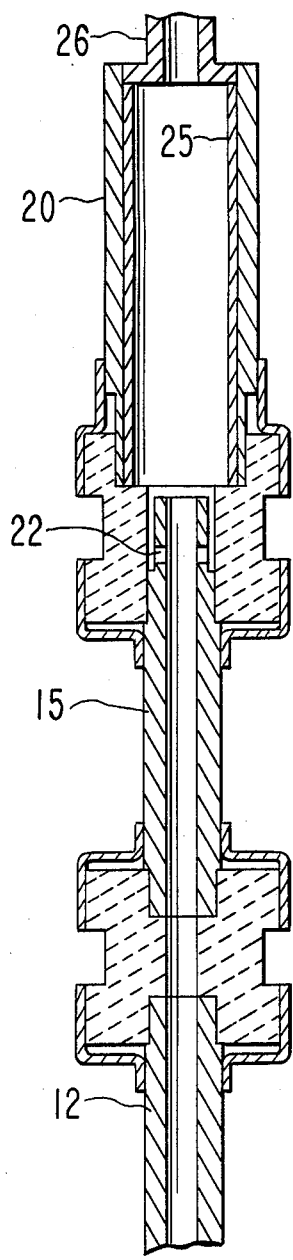
FIG. 1 is a schematic cross-sectional view of an electron capture detector with which the bipolar pulsing method of the present invention may be used.

In one aspect of the present invention, methods are provided for operating pulsed ECDs so as to disperse the space charge sheath believed to become established near the anode of the ECD when it is operated at a high frequency in a conventional unipolar mode. Stated briefly, the present invention accomplishes this objective by operating the ECD in a bipolar mode, or by using an additional pulse of opposite polarity with respect to the initial extraction pulse. This may be done, for example, by using an ECD of the conventional type shown in FIG. 1 wherein the sample with carrier and/or make-up gas travels from an inlet tube 12 through a cylindrical anode 15 which is insulated therefrom. At the top, the anode 15 is provided with side ports 22 and opens into a cylindrical cell 20. The cell 20 and the anode 15 are insulated from each other. On the inner wall of the cell 20 is a radioactive foil 25, while the top of the cell 20 is connected to an exit tube 26.

Figure 2:
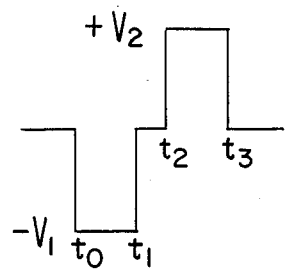
FIG. 2 is a typical bipolar pulse which may be applied to the electrode of ECD in FIG. 1.

FIG. 2 shows a typical way in which pulses may be applied to the cell 20 of FIG. 1 according to the present invention, i.e., a standard pulse (negative and of magnitude $V_1$) followed by a second pulse (positive and of magnitude $V_2$). Modes wherein $t_2 = t_1$ should also be considered within the purview of the present invention.

Figure 3:
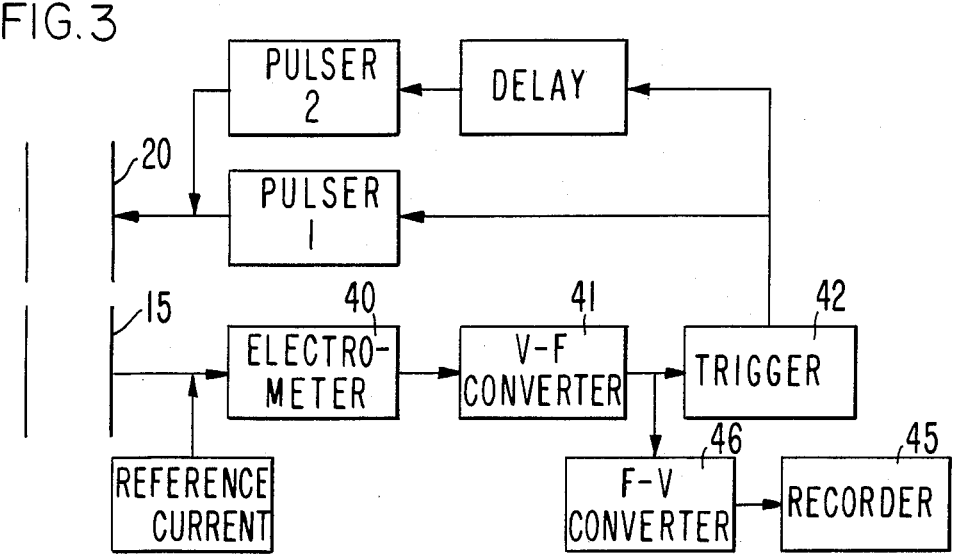
FIG. 3 is a block diagram of electronic components for providing bipolar pulsing to ECD of FIG. 1 according to the present invention.

FIG. 3 is a block diagram showing how the electronic components may be arranged for operating the ECD of FIG. 1 in a bipolar mode with pulse profile given by FIG. 2. A reference current, as explained in the aforementioned reference by Maggs, et al, is compared with the current from the collector (anode) 15. It is generally so adjusted that the sum of the reference current and the (negative) current from the collector will be maintained at zero. When an electron-capturing species enters the detector (cell 20), the collector current tends to decrease and a current is produced and detected by the electrometer 40. In order to maintain the aforementioned zero-current condition, the frequency of the applied pulse must be changed. This change is effected by the voltage (V) to frequency (F) converter 41 and the trigger 42 for pulser 1 and pulser 2 for generating pulses $V_1$ and $V_2$ of FIG. 2, respectively. The effected frequency changes are recorded by a recorder 45 connected through a F-V converter 46 in a known way.

Figure 4:
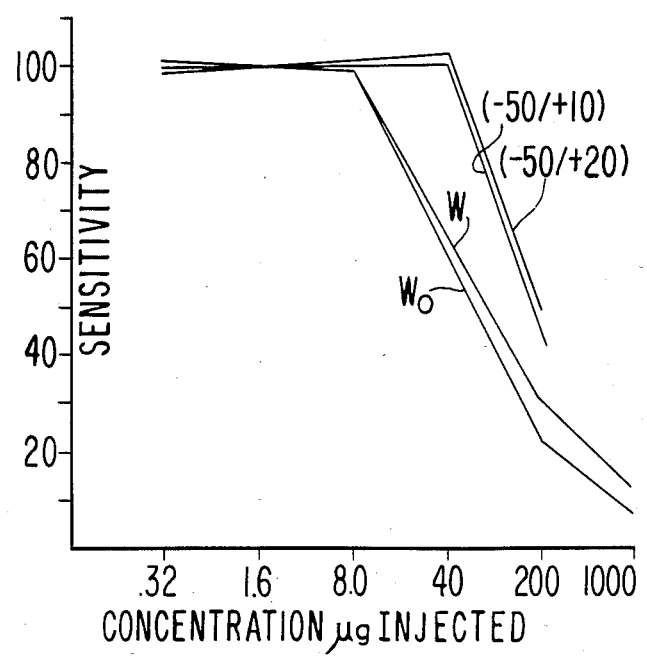
FIG. 4 shows the enhancement of linear dynamic range by the bipolar pulsing technique of the present invention.

FIG. 4 shows graphically by means of a sensisivity-to-concentration curve the achieved enhancement in linear dynamic range by the single-electrode bipolar pulsing scheme described above. The various curves therein reflect comparisons of the response of the ECD. The curve marked WO with a smaller linear range corresponds to a unipolar case with a 600 ns, $-50$ V pulse. The curves marked $(-50/+10)$ and $(-50/+20)$ represent a situation where the standard 600 ns, $-50$ V pulse is followed immediately by a 600 ns, $+10$ V and 600 ns, $+20$ V pulse, respectively. Comparison of the bipolar $(-50/+10)$ and $(-50/+20)$ curves with the standard-electronics curve WO clearly shows that both the dynamic range and the linearity of the ECD can be extended with the bipolar mode.

Figure 5:
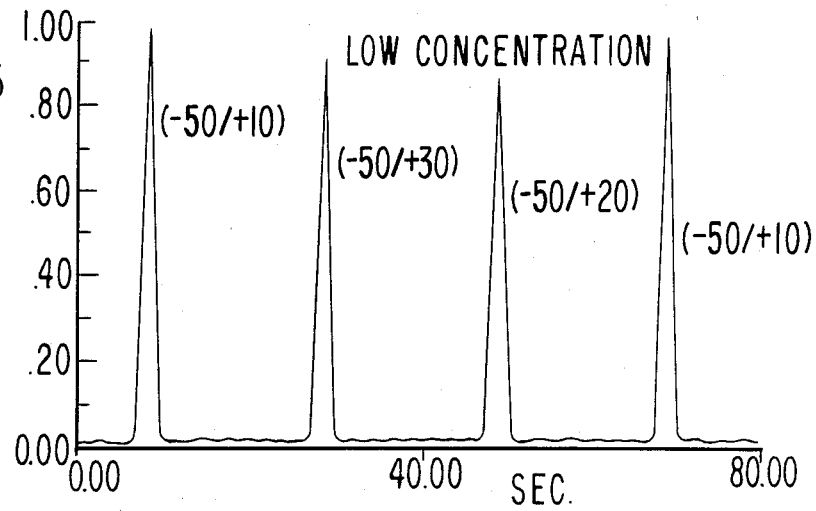
FIG. 5 shows the relationship between peak shape and the pulser voltage at low concentration.

Examination of peak height as function of sample concentration for several base frequencies and bipolar pulse profiles reveals that the sensitivity is strongly dependent on base frequency at low concentrations and that the bipolar scheme enhances dynamic range and linearity at high concentrations. Peak shapes are nearly identical at low frequencies as shown in FIG. 5, the linear behavior of the bipolar pulse mode being largely independent of the pulser voltage amplitude. Peak ($-50/+30$) similiarly represents a situation where a 600 ns, $+30$ V pulse follows the standard negative extraction pulse immediately.

Figure 6:
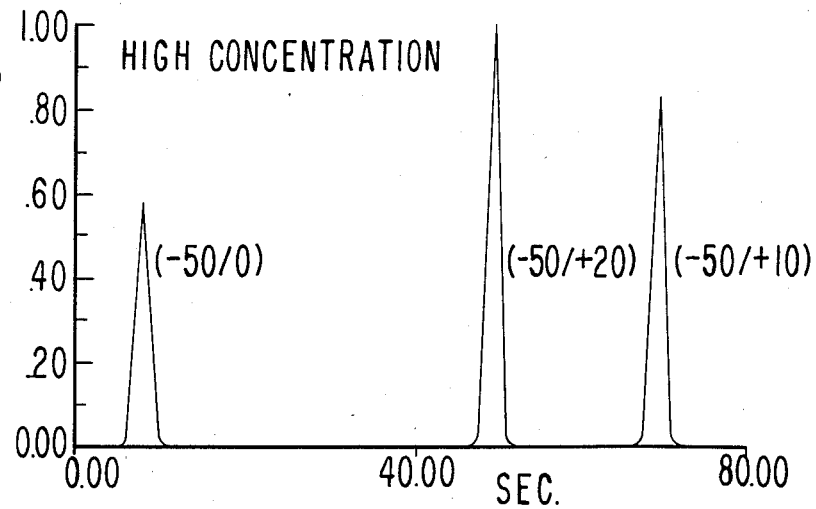
FIG. 6 shows the relationship between peak shape and the pulser voltage at high concentration.

At high frequencies (or concentrations), by contrast, it is observed (as in FIG. 6) that the peak height is strongly dependent on the repulser voltage amplitude. An increase in peak height by nearly 40% is observed in the case of FIG. 6 when $V_2 = 20$ V as compared to when only the $-50$ V pulser is operating, as per the conventional unipolar mode. The result is a significant drop in response when not operating in the bipolar mode.

There is another method for extending the linear dynamic range to higher concentration by using the so-called voltage fold-back technique, which is to reduce the extraction voltage as a function of increasing frequency. In FIG. 2, curve W shows results which are comparable to curve WO except it is by the standard electronics having voltage fold-back. The other curves in FIG. 2 were obtained without voltage fold-back. Judicious choice of the fold-back frequency and rate of fold-back may thus be expected to allow greater control at high frequencies while still maintaining other purposes of voltage fold-back such as protection against short-circuiting of the power supply and pulsing circuits and protection of the operator from severe electrical shocks.

The bipolar pulsing technique has been applied above to a single-electrode ECD. The technique, however, may also be used with ECDs having separate electrodes. Two examples of such ECD design are shown in FIGS. 7 and 8 wherein parts corresponding to those in FIG. 1 are assigned the same numerals. In FIG. 7, a secondary ring-shaped electrode 30' is insulated and/or separated both from the anode 15' and the cell 20' and is placed near the top of the cylindrical anode 15'. According to the design shown in FIG. 8, the ECD is provided with a structure 35" having a cup-shaped end section as disclosed in U.S. patent application Ser. No. 522,081, now abandoned, filed Aug. 11, 1983 by one of the present inventors and assigned to the present assignee. The structure 35", besides being a secondary electrode so that it must be electrically insulated from the cell 20", therefore, serves to separate the active volume from the areas at the top corners of the cell 20". FIGS. 7 and 8 additionally show how pulses may be applied to the electrodes.

FIG. 9 is another block diagram showing how the electronic components may be arranged for operation of an ECD of the type having separate electrodes (20' and 30', or 20" and 35") connected to pulser 1 and pulser 2, respectively. In general, there are four possible orientations for bipolar pulsing. They are: (1) a negative pulse from one pulser and a positive pulse from the other; (2) a negative pulse from one pulser and a negative pulse from the other; (3) a positive pulse from one pulser followed by a negative pulse from the other; and (4) a positive pulse from one pulser followed by another positive pulse from the other. These pulse profiles are illustrated in FIG. 10 together with the arrangements of electronic components for effecting the desired pulsing scheme. Specific details regarding pulse widths, and particulars, base frequency, reference current, foil loading, etc. should be optimized for the specific ECD geometry and chromatographic applications.

The present invention has been described above in terms of only a limited number of embodiments, but they are intended to be illustrative, rather than limiting, and should be construed broadly. For example, designs of the ECD are not limited to those explicitly illustrated in the figures. When separate electrodes are used for the application of two pulses in particular, the second electrode (for second pulse) may be shaped and/or positioned differently from the drawings as long as the desired objective of dispersing the charged sheath near the anode is effectively accomplished. A structure similarly shaped and positioned as the secondary electrode 35" of FIG. 8 may be inserted even if it is not connected to either of the pulsers, but entirely for the purpose described in the aforementioned, i.e., U.S. patent application Ser. No. 522,081. The tubular anode 15 (as well as 15' and 15") may have an insulative surface as shown in U.S. patent application Ser. No. 529,291 filed Nov. 10, 1983 by one of the present applicants and assigned to the present assignee. As for the bipolar pulse in itself, the relative intensity, duration, polarity and timing of the two pulses may be changed freely from those illustrated, as explained above. The scope of the invention is limited only by the following claims.

What is claimed is:

1. An electron capture detector comprising:
means defining a detection volume for accepting a carrier gas and a vaporized sample to be analyzed;
an anode communicating with said detection volume;
means for continuously ionizing said carrier gas to continuously produce free electrons in said volume, said free electrons being available for attachment to said sample to produce anions;
means for applying to said detection volume a first electric pulse to move electrons toward said anode;
means for applying to said detection volume a second electric pulse following said first pulse sufficient to disperse anions away from said anode, but insufficient to clear said detection volume of said anions.

2. A detector as in claim 1 in which said second pulse is no greater than said first pulse in amplitude.

3. A detector as in claim 1 in which said second pulse is no greater than said first pulse in duration.

4. A detector as in claim 1 in which said second pulse is less than said first pulse in either duration or amplitude or both.

5. The detector of claim 1 which further includes a first conductive member cooperating with said anode to define said active detector volume therebetween.

6. The detector of claim 5 in which said first conductive member is of hollow generally cylindrical form enclosing said active detection volume.

7. The detector of claim 6 in which said anode is tubular and opens into said first conductive member.

8. The detector of claim 5 in which a source of gamma radiation is affixed to said first conductive member so as to irradiate said detection volume.

9. The detector of claim 5 in which said first and second pulses are applied between said anode and first conductive member.

10. The detector of claim 5 in which said first and second pulses are applied to said conductive member.

11. The detector of claim 5 further including a second conductive member electrically insulated from both said anode and from said first conductive member.

12. The detector of claim 11 in which said second conductive member has a one-shaped section, said first conductive member forming a hollow enclosure, said second conductive member being disposed within said first conductive member.

13. The detector of claim 11 in which one of said pulses is supplied to said anode, while the other is supplied to said second conductive member.

14. The detector of claim 11 in which said second conductive member is ring-shaped and is disposed adjacent to and in alignment with said anode.

15. The detector of claim 1 in which said first pulse is negative, and said second pulse is positive.

16. The detector of claim 1 in which said first and second pulses are applied to said anode.

17. An electron capture detector with an increased linear dynamic range when operated in constant current mode, comprising:
   electrode means defining an active detection volume, said means including an anode and a first conductive member, said detection volume accepting a carrier gas and a vaporized sample;
   means for continuously ionizing said carrier gas to produce electrons resulting in an anode current, said sample absorbing electrons and forming anions; and
   means for applying successive electric pulse pairs to said electrode means, first ones of each pulsed pair influencing the electrons and anions in opposite manner to said second ones of each said pair, the frequency of application of said pulses being varied to maintain constant said anode current.

18. A detector as in claim 17 in which first ones of said pulsed pairs move electrons toward said anode, while second ones of said pulsed pairs are sufficient to disperse anions away from said anode.

19. A detector as in claim 17 in which said second ones of said pulsed pairs are less than said first ones of said pulsed pairs either in amplitude or duration or both.

20. A detector as in claim 17 in which said means for applying successive pulses applies said pulses to said anode.

21. A detector as in claim 17 in which said means for applying pulses applies said pulses to said conductive member.

22. A detector as in claim 17 in which first ones of said pulse pairs are applied to said anode, while second ones of said pulse pairs are applied to said conductive member.

23. A detector as in claim 17 in which said first conductive member is of hollow generally cylindrical form enclosing said active detection volume.

24. A detector as in claim 17 in which said electrode means further includes a ring-shaped metallic auxilliary electrode adjacent said anode and aligned therewith, and electrically insulated from both said anode and said first conductive member.

25. A detector as in claim 24 in which one pulse of said pulse pairs is applied to said anode, while the other pulse of said pulse pairs is applied to said ring-shaped auxilliary electrode.

26. A detector as in claim 17 in which said electrode means further includes a cup-shaped metallic auxilliary electrode spaced from said anode and aligned therewith, and electrically insulated from both said anode and said first conductive member.

27. A detector as in claim 26 in which one pulse of said pulse pairs is applied to said anode, while the other pulse is applied to said cup-shaped electrode.

28. A detector as in claim 17 in which one pulse of said pulse pairs is negative.

29. A detector as in claim 28 in which the other of said pulse pairs is positive.

30. A detector as in claim 17 in which both pulses of said pulse pairs are of the same polarity.

* * * * *